United States Patent [19]
Kherani

[11] Patent Number: 6,159,427
[45] Date of Patent: Dec. 12, 2000

[54] APPARATUS FOR TRITIUM-IN-WATER MONITORING

[75] Inventor: Nazir P. Kherani, Toronto, Canada

[73] Assignee: Ontario Power Generation Inc., Toronto, Canada

[21] Appl. No.: 09/293,996

[22] Filed: Apr. 19, 1999

[51] Int. Cl.[7] ................................................ G01N 33/20
[52] U.S. Cl. .......................... 422/82.01; 422/98; 436/39; 436/57; 436/181
[58] Field of Search .................... 422/82.01, 98; 436/39, 57, 144, 181

[56] References Cited

U.S. PATENT DOCUMENTS

| | | |
|---|---|---|
| 3,489,903 | 1/1970 | Robinson . |
| 3,655,982 | 4/1972 | Gelezunas . |
| 4,019,864 | 4/1977 | Saito et al. . |
| 4,445,037 | 4/1984 | Anderson . |
| 4,464,338 | 8/1984 | Dotson et al. ........................... 422/78 |
| 4,755,471 | 7/1988 | Saito et al. ............................. 436/57 |
| 4,766,081 | 8/1988 | Ruckert ................................. 436/144 |
| 5,661,299 | 8/1997 | Purser . |
| 5,783,828 | 7/1998 | Pacenti et al. . |
| 5,939,330 | 8/1999 | Peterson ............................... 436/180 |

OTHER PUBLICATIONS

Hofstetter, K.J., Wilson, H.T., "Aqueous tritium detection using immiscible liquid scintillation cocktails", in *Transactions of the American Nuclear Society*, vol. 64 (1991) 17–20.

Rapkin, E., Gibbs, J.A., "A system for continuous measurement of radioactivity in flowing streams", *Nature* 194 (4823)(1962) 34–36.

Cuttler, J.M., Mina, N., Swami, L., Ely, F.A., "Monitoring CANDU service water discharge for tritium" *Tropical meeting on Environmental Transport and Dosimetry*, ANS (1993) 95–97.

Osborne, R.V., "Detector for tritium in water", *Nuclear Instruments and Methods* 77 (1970) 170–172.

Singh, A.N., Ratnakaran, M., Vohra, K.G., "An on–line tritium–in–water monitoring", *Nuclear Instruments and Methods in Physics Research A236* (1985) 159–164.

Hofstetter, K.J., "Development of aqueous tritium effluent monitor", in *Liquid Scintillation Counting and Organic Scintillators*, Lewis Publishers Inc. (1991) 421–433.

Hofstetter, K.J., Wilson, H.T., "Aqueous effluent tritium monitor development", *Fusion Technology 21* (1992) 446–451.

Rucker, T.L., Ross, H.H., Schweitzer G.K., "Monte Carlo modeling of fiber–scintillator flow–cell radiation detector geometry", *Nuclear Instruments and Methods in Physics Research A267* (1988) 511–519.

(List continued on next page.)

*Primary Examiner*—Jeffrey Snay

[57] ABSTRACT

A method and apparatus for in-line tritium-in-water monitoring in which a sample of water is vaporized at a temperature sufficient to transform it to dry water vapor substantially free of liquid water droplets. The water vapor is transferred to a tritium detection device having a chamber heated to a temperature at which there is substantially no condensation of the water vapor, the detection device comprising volume detection device adapted to detect β-decay of tritium atoms in the water vapor. The volume detection device may comprise ionization chamber detector, gas scintillation counting detector and gas electron multiplier detector. The method and apparatus are preferably used to detect leaks of tritiated water from the primary to secondary side of the heat transport systems associated with certain types of nuclear reactors, and when used on an in-line, continuous basis, provide a time response as low as 10 seconds with the detection limits depending on the type of volume detection equipment used. This method also lends itself to in-line monitoring of tritium in water discharged to lakes, rivers and sewers, and may also be amenable to environmental monitoring of tritium in waterways.

7 Claims, 7 Drawing Sheets

OTHER PUBLICATIONS

Budnitz, R.J., "Tritium instrumentation for environmental and occupational monitoring—a review", *Health Physics 26* (1974) 165–178.

Campi, F., Mascherpa, C., Sterlini, C., Pacenti, P., Terrani, S., "A gas scintillation monitor for tritium gas in argon or in nitrogen", *Health Physics 71* (3) (1996) 335–339.

Sauli, F., "GEM: A new concept for electron amplification in gas detectors", *Nuclear Instruments and Methods in Physics A 386* (1997) 531–534.

Bouclier, R/., Dominik, W., Hoch, M., Labbé, J.C., Million, G., Ropelewski, L., Sauli, F., Sharma, A., Manzin, G., "New observations with the gas electron multiplier (GEM)", *Nuclear Instruments and Methods in Physics Research A 396*(1997) 50–66.

Büttner, C., Capeáns, Dominik, W., Hoch, M., Labbé, J.C., Manzin, G., Million, G., Ropelewski, F., Sauli, F., Sharma, A., "Progress with gas electron multiplier", *Nuclear Instruments and Methods in Physics Research A 409*(1998) 79–83.

Sepall, O., Mason, S.G., "Vapor/liquid partition of tritium in tritiated water", *Can. K. Chem 38* (1960) 2024–2025.

"Average energy required to produce an ion pair", *International Commission on Radiation Units and Measurements, ICRU Report 31* (1979).

Kherani, N.P., Shmayda, W.T., "In–line process tritium monitors", *Fusion Technology 21* (1992) 340–345.

Kherani, N.P., Shmayda, W.T., HTO monitoring using heated ion chambers, *IEEE/NPSS 15th Symposium on Fusion Eng.*, Hyannis, MA. (Oct. 1993) 80–84.

Test 1: Tritium-in-water monitoring using water vapour and a heated, in-line, ionization chamber Test 3: Tritium-in-water monitoring using water vapour and a heated, in-line, ionization chamber

APPARATUS FOR TRITIUM-IN-WATER MONITORING

FIELD OF THE INVENTION

The present invention relates to an improved method and apparatus for measuring tritium levels in water, and particularly to such a method and apparatus in which the water sample is vaporized to water vapor. The method and apparatus of the present invention are particularly adapted to in-line monitoring of tritium levels in water.

BACKGROUND OF THE INVENTION

Tritiated water, or super-heavy water, can be denoted as HTO or $T_2O$, where T refers to tritiumn, an elemental hydrogen isotope having three neutrons in its nucleus. The compound $T_2O$ is unstable in water, and generally forms HTO. Tritium decays by emitting β particles (electrons), a form of radiation which is potentially harmful due to its ability to ionize living matter.

Tritiated water is a by-product of nuclear power generation, being produced in the primary heat transport systems of certain types of nuclear reactors, such as CANDU reactors. In such reactors, heat is transferred from the primary heat transport system to a secondary heat transport system, both of which are closed systems, via a heat exchanger. The heat transferred from the primary system to the secondary system is used to generate steam in the secondary system, and excess heat is then removed from the water in the secondary system by service water brought in from a body of water located adjacent to the power station. The heated process water is then returned to the body of water.

Occasionally, tritiated water leaks from the primary to the secondary heat transport system. It is preferred that such leaks are quickly detected and corrected in order to minimize heat loss and also to prevent tritium contamination of the water in the secondary system, thereby minimizing the likelihood that tritiated water could be released into the environment in the discharged service water. Therefore, tritium levels in the secondary heat transport systems of nuclear plants are routinely monitored to detect leakage of tritiated water from the primary to the secondary heat transport systems.

Currently, the most effective method for monitoring tritium levels in waste water is liquid scintillation counting (LSC). The detection limit of LSC is quite low, of the order of tens of nCi/L which can potentially allow detection of a leak from the primary to the secondary heat transport systems in CANDU reactors of the order of 0.1 L/h. In LSC, a sample of potentially tritiated water is mixed with a liquid scintillant and the mixture is then monitored for photoactivity with the aid of one or more photomultipliers. Specifically, the liquid scintillant effectively surrounds each water molecule such that a β particle emitted by a tritiated water molecule excites the scintillant, causing the scintillant to emit a photon which is detected by the photomultipliers.

LSC monitoring is frequently referred to as "grab sampling", with a typical nuclear power station collecting and analyzing up to 40 to 50 sample vials each day from the secondary heat transport system, which is quite labour intensive and does not permit leaks to be detected quickly. An automated version of LSC is known which monitors tritium-in-water levels on a semi-continuous basis. One major disadvantage of LSC is that particulate and biological matter removed from the water sample by filtration frequently cause fouling of the filter element, resulting in high maintenance costs. Further, the organic scintillant combined with the tritiated water sample in LSC cannot be returned to the environment, and therefore the LSC samples must be disposed of as low level radioactive waste.

A less common method for tritium monitoring is solid scintillation counting (SSC). In SSC, a sample of water is passed between two closely spaced sheets of plastic containing a solid scintillant. The β particles produced by the decay of tritium atoms in a thin layer of water immediately adjacent each sheet are deposited on the solid scintillant, which in turn emits a photon to be detected by a photomultiplier. SSC is fundamentally less efficient than LSC because it relies on surface detection while LSC is based on volume detection. Automated SSC detector systems have demonstrated detection limits around 1 $\mu$Ci/L.

SSC also requires filtration and is therefore subject to the same disadvantage as LSC in regard to filter fouling. In addition, SSC is subject to memory effects from tritium retention on the solid scintillant, thereby reducing its effectiveness.

Clearly, a more effective method for monitoring tritium levels in water is needed.

Some of the above disadvantages of current methods for monitoring tritium levels in water may partially be overcome by the method disclosed in U.S. Pat. No. 3,489,903, issued Jan. 13, 1970 to Robinson. This patent describes a method of measuring tritium levels in a sample of urine in which a known volume of tritium-contaminated urine is vaporized in a confined zone such as an ionization chamber. The β particles produced by tritium decay traverse the ion chamber, producing a number of ionizations which are measured as a current signal in the ionization chamber. One of the primary advantages of this method is that it allows rapid measurement of tritium levels in a liquid sample.

The apparatus described by the Robinson patent is adapted to determine whether or not the tritium level in the urine exceeds a maximum acceptable tolerance of 50 $\mu$Ci/L. To the inventor's knowledge, it has not been adapted to use in detecting leaks of tritiated water from nuclear reactors. In any event, the sensitivity of the Robinson method would likely not be acceptable for leak detection in a nuclear power plant, since the detection limit of 50 $\mu$Ci/L disclosed by Robinson translates to a leak of about 100 L/h from the primary to the secondary heat transport systems in a CANDU reactor, which is substantial.

It would be desirable to provide a simple and effective method for tritium-in-water monitoring which is capable of quickly detecting low levels of tritium in a sample of water to thereby provide fast and effective detection of leaks in a nuclear reactor.

SUMMARY OF THE INVENTION

The present invention provides a method and apparatus for measuring tritium content in a sample of water which overcomes many of the disadvantages of the prior art discussed above. Like the Robinson patent, the method and apparatus of the present invention first vaporizes a sample of tritium-containing water and then measures the tritium content with a volume detection device, thereby overcoming the disadvantages of LSC and SSC discussed above. However, the method and apparatus of the present invention are capable of providing a more accurate measurement than the apparatus and method disclosed by Robinson, are capable of measuring tritium levels substantially lower than the maximum acceptable tolerance of 50 $\mu$Ci/L disclosed by Robinson, and overcomes the fouling issues such as related with service water in nuclear systems.

The present invention results partially from the inventor's discovery that, although sample vaporization overcomes disadvantages of LSC and SSC, it does not necessarily provide accurate measurement of tritium levels when the tritium level of the vapor is measured by volume detection devices. Specifically, the inventor has discovered that the accuracy of tritium measurement in the vapor phase is negatively affected by the presence of liquid water droplets in the vaporized sample, and that liquid water droplets may be present in the vapor at temperatures substantially greater than the boiling point of water.

The negative effect of liquid water droplets on the accuracy of tritium measurement may be explained as follows. The β particles produced via tritium decay have a much greater range in air, about 6 mm, than in water, about 3 to 5 μm. A typical water droplet present in the vaporized sample has a diameter of the order of microns. Therefore, some of the β particles emitted by tritium atoms in the droplet will not escape the droplet to be released into the gas phase, and will therefore not be detected. This results in an inaccurate measurement of the tritium level in the vaporized sample as well as an attenuated signal.

Robinson discloses that the temperature should be sufficient to vaporize water, that is at or above 100° C. However, the inventor has found that significant amounts of water droplets may remain in the liquid sample even at temperatures substantially greater than 100° C., resulting in reduced sensitivity of the detection device. This effect would likely go unnoticed in the Robinson method, which is adapted to measure relatively high tritium levels.

The method according to the present invention is expected by the inventors to allow detection of tritium levels in water at least as low as 250 nCi/L, which is at least two orders of magnitude more sensitive than the test discussed in the Robinson patent, and approaches the level of sensitivity achieved by LSC. This translates to a water leak of about 0.5 L/h from the primary to the secondary heat transport system in a CANDU reactor.

The present invention also provides for the first time an in-line method and apparatus for tritium-in-water monitoring which provides almost instantaneous measurement of tritium levels in water flowing through a conduit, for example in the detection of leaks from the primary to the secondary heat transport systems in a CANDU reactor, and service water from a nuclear reactor being discharged into the environment. The in-line method and apparatus of the invention are capable of reducing the time response of tritium monitoring to as low as about 10 seconds.

Accordingly, in one aspect the present invention provides a method for measuring tritium content of a quantity of water, said method comprising: vaporizing said quantity of water at a temperature sufficient to transform said quantity of water to dry water vapor substantially free of liquid water; and transferring said water vapor to a tritium detection device having a chamber heated to a temperature at which there is substantially no condensation of said water vapor inside said chamber, wherein said tritium detection device comprises volume detector adapted to detect β-decay of tritium atoms in dry water vapor and wherein said tritium detection device generates a signal which is representative of a concentration of said tritium content of said quantity of water.

In another aspect, the present invention provides an apparatus for continuously monitoring tritium content in a stream of water flowing through a conduit, said apparatus comprising: (a) an inlet connected to said conduit, said inlet adapted to receive a portion of said stream of water from said conduit; (b) centrifuging means connected to said inlet for centrifuging said portion of said stream of water diverted from said conduit; (c) aspirating means adapted to generate a mist of water from said portion of said stream of water being centrifuged; (d) heated conduit means having a first end and a second end, said first end adapted to receive said mist from said aspirating means, said conduit means being heated to a temperature sufficient, and being of sufficient length, to convert said mist to a dry water vapor containing substantially no liquid water as it passes from said first end to said second end; (e) a gas vortex connected to said second end of said heated conduit means and being adapted to remove residual water droplets from said water vapor; (f) tritium detection means comprising a volume detection device adapted to detect β-decay of tritium atoms in said water vapor and to generate a signal which is representative of said tritium content of said stream of water flowing through said conduit, said tritium detection means comprising a chamber having an inlet and an outlet, said inlet receiving said dry water vapor from said gas vortex, said chamber being heated to a temperature at which there is substantially no condensation of said water vapor inside said chamber; (g) condenser means receiving said water vapor from said tritium detection means and cooling it to a temperature at which it is condensed to liquid water; and (h) outlet means through which condensed water leaves the apparatus.

BRIEF DESCRIPTION OF THE DRAWINGS

The present invention will now be described, by way of example only, with reference to the accompanying drawings, in which.

DETAILED DESCRIPTION OF PREFERRED EMBODIMENTS

Figure 1:
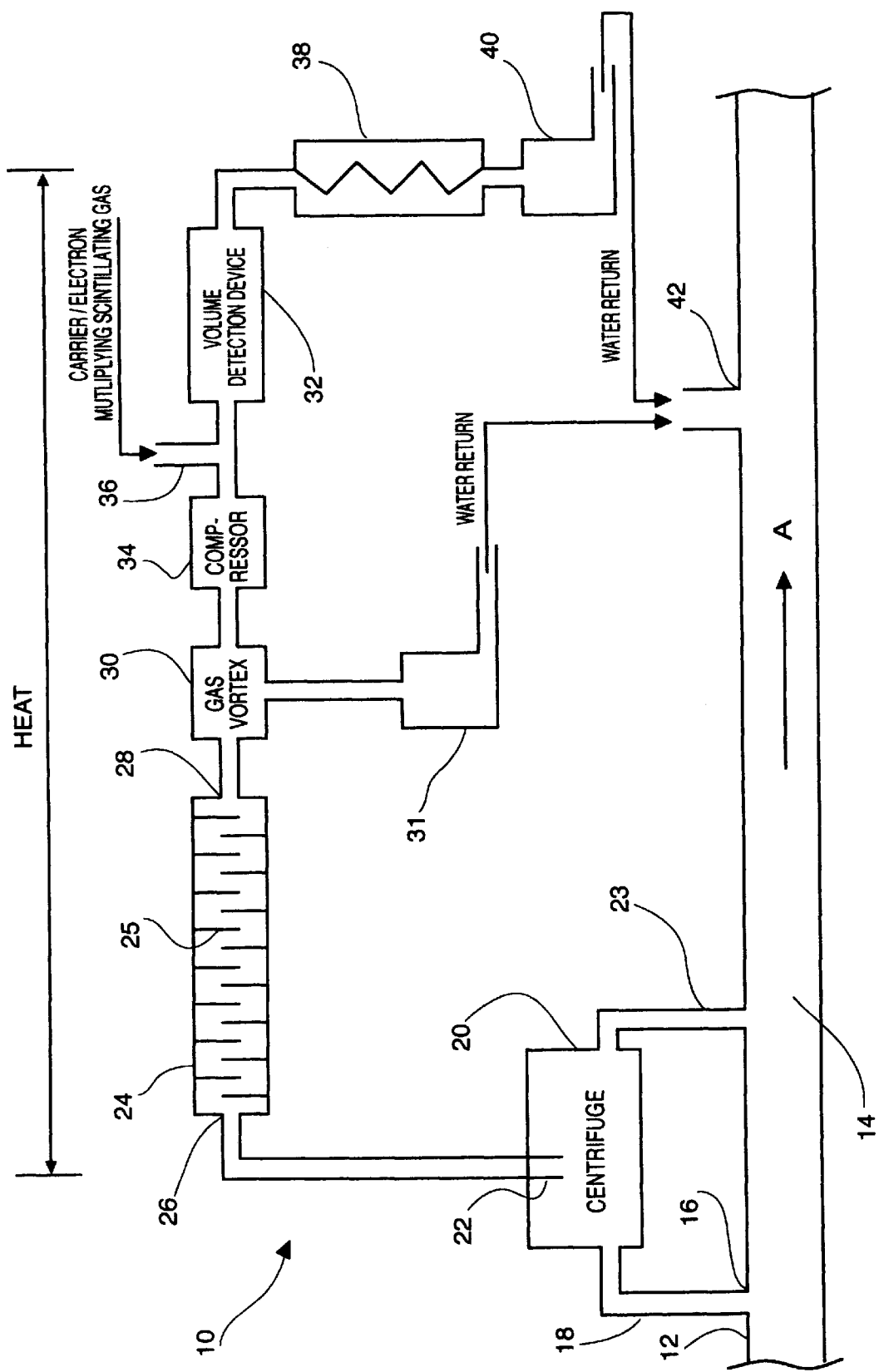
FIG. 1 is a schematic diagram of a preferred apparatus for in-line tritium monitoring.

A particularly preferred method and apparatus for in-line, continuous tritium-in-water monitoring is now discussed below with reference to FIG. 1, comprising a schematic diagram of a particularly preferred apparatus 10 according to the present invention.

Apparatus 10 is connected to a conduit 12 through which a stream of water 14 is flowing in the direction of arrow A. Apparatus 10 has an inlet 16 in communication with conduit 12, the inlet 16 being adapted to receive a portion of the stream of water 14 from conduit 12. From the inlet 16, water flows through inlet pipe 18 to a centrifuge 20.

The water is centrifuged to separate particulate matter from the water to be analyzed by causing particulate matter in the water to move outwardly from the center of the liquid being centrifuged. At the center of the centrifuging liquid is an aspirator 22 which creates a mist of finely divided water droplets which then flow into a heated pipe 24. It will be appreciated that the amount of water taken into pipe 24 through aspirator 22 is a small fraction of the amount of water which enters centrifuge 20. Therefore, a water return pipe 23 is preferably provided through which excess water is returned from centrifuge 20 to conduit 12. It will also be appreciated that the flow of water to and from centrifuge 20 is continuous.

The heated pipe 24 is preferably provided with baffles 25 on its interior surface. The heated pipe 24 has first and second ends 26 and 28, respectively, the first end being joined to the aspirator 22 to receive the water mist therefrom. Pipe 24 is heated to a sufficient temperature, and is of sufficient length, such that the water mist entering first end 26 of pipe 24 is substantially completely vaporized to dry water vapor by the time it reaches the second end 28 of pipe 24. Preferably, the temperature of heated pipe 24 is greater than about 170° C., and is even more preferably at least about 250° C. Most preferably, the temperature of heated pipe 24 is 250° C.

In order to ensure that the water vapor contains substantially no liquid water, the second end 28 of heated pipe 24 is preferably connected to a gas vortex 30 which spins out any water droplets remaining in the water vapor, thereby producing dry water vapor. It will be appreciated that gas vortex 30 is not an essential component of the apparatus of the invention. In some embodiments, the heated pipe 24 may be of sufficient length and temperature such that substantially no liquid water is present in the vapor as it exits the second end 28 of pipe 24. The water droplets removed from the water vapor by the gas vortex 30 is preferably collected in a trap 31 for eventual return to conduit 12.

From the gas vortex 30, the dry water vapor is then passed to an in-line volume detection device 32 adapted to detect β-decay of tritium atoms in the water vapor and to generate a signal which is representative of the tritium content in the water vapor, and consequently in the stream of water flowing through the conduit 12. The volume detection device may be one of several types presently known, including ionization chamber detectors, an example of which is disclosed by the Robinson patent; gas scintillation counting detectors such as that described in U.S. Pat. No. 5,783, 828, issued on Jul 21, 1998 to Pacenti et al.; and proportional detectors. Any of these detectors may additionally comprise a gas electron multiplier, in which gas ionizations are multiplied by the placement of strategic electrodes creating high electric fields, thus lowering the detection limit. Gas electron multipliers are discussed by F. Sauli in "GEM: A new concept for electron amplification in gas detectors", *Nuclear Instruments and Methods in Physics Research A*386 (1997) 531–534; by Bouclier et al. in "New observations with the gas electron multiplier (GEM)", *Nuclear Instruments and Methods in Physics Research A*396 (1997) 50–66; and by B üttner et al. in "Progress with gas electron multiplier", *Nuclear Instruments and Methods in Physics Research A*409 (1998) 79–83.

It may be preferred in some embodiments of the invention to increase the pressure of the dry water vapor entering the chamber of the volume detection device 32. As discussed below, raising the pressure of the water vapor lowers the detection limit. More preferably, the pressure is increased to the range of from about 1 to about 3 atmospheres by a compressor 34 as schematically shown in FIG. 1. It will be appreciated that increasing the pressure of the water vapor may necessitate raising the temperature in order to avoid condensation of water vapor inside the chamber.

The chamber of the detection device 32 is maintained at a temperature at which there is substantially no condensation of the water vapor inside the chamber. It may be preferred that the temperature inside the chamber is maintained at about the same temperature as the heated pipe 24, however this is not necessarily the case. The inventor has found that, as long as the water vapor entering the chamber contains substantially no water vapor, there will be no appreciable amount of condensation inside the chamber so long as the chamber is maintained at a temperature substantially greater than the boiling point of water, i.e. 100° C., and preferably greater than 170° C.

Where the volume detection device 32 comprises a gas ionization detector, β particles released from tritium atoms inside the chamber traverse the chamber, having a range of about 6 mm, causing the production of electron ion pairs in the chamber. The electron ion pairs produced by the β particles are separated by the electric field between two electrodes, one of which is a collector located in the center of the chamber, and the other of which is typically provided by the walls of the chamber, thus giving rise to a measurable electric current.

Where the volume detection device comprises a gas scintillation counting detector, a feed line 36 is provided which adds a scintillating gas, such as nitrogen, argon or helium to the sample being analyzed. The scintillating gas is preferably preheated before being added to the dry water vapor immediately before it enters the chamber of the volume detection device 32. However, it will be appreciated that the scintillating gas may instead be added prior to this point, for example it may be added to the water mist before it enters the heated pipe 24.

The chamber of the gas scintillation counting detector contains a number of UV sensitive photomultiplier tubes. The β particles emitted by tritium inside the chamber excite the scintillating gas atoms, which then emit photons which are detected by the photomultiplier tubes via viewports on the chamber.

After passing through the detection chamber of the volume detection device 32, the water vapor is passed through a condenser 38 which cools the water vapor to a temperature at which it is condensed to liquid water. Preferably, the condensed water is collected in a trap for eventual return to the stream of water 14 in conduit 12, for example through outlet 42 which, as shown in FIG. 1, also returns to conduit 12 the liquid water removed from the vapor by gas vortex 30.

Having now described a preferred method and apparatus according to the invention, the following is a description of the theory behind the gas phase monitoring of tritium content in a sample of water vapor according to the invention. The following description makes reference to gas ionization as the volume detection method. However, it will be appreciated that any of the volume detection devices described above could be used.

According to the principle of gas ionization, the saturated current $i_s$ resulting due to the presence of a tritium concentration of $c_g$ in a detection volume V can be expressed as $$i_s = \frac{c_g V \lambda E_m e}{W_{H_2O}} \quad (1)$$

where λ is the tritium decay rate constant, $E_m$ is the mean tritium decay beta energy, $W_{H_2O}$, which is usually referred to as the W value, is the mean energy expended by the emitted beta radiation to form an ion pair in water vapor, and e is the electronic charge.

Using the definition $$c_g \equiv \frac{N_{HTO}}{V} \qquad (2)$$

where $N_{HTO}$ represents the number of vaporized HTO molecules present in the detection volume V, equation 1 can be expressed as follows:

$$i_s = \frac{N_{HTO} \lambda E_m e}{W_{H_2O}}. \qquad (3)$$

Tacit in the above relation is the presence of dry water vapor in volume V at a pressure p which exceeds the threshold pressure above which the saturated current is unaffected by variations in pressure and less than an upper pressure limit beyond which charge recombination effects become significant. The above relationship represents a correspondence between the saturated current, which is approximated by the net measured current, and the number or activity of vaporized HTO molecules in the ionization chamber detection volume. Defining the quotient of the saturated current and the number of vaporized HTO molecules as the specific saturated current, we obtain the following:

$$I_{HTO/H_2O} \equiv \frac{i_s}{N_{HTO}} = \frac{\lambda E_m e}{W_{H_2O}}. \qquad (4)$$

The specific saturated current, $I_{HTO/H_2O}$, is a constant determined by the decay rate and mean beta energy of tritium and the ionization property of water vapor. The measurable signal current, i, which approximates the saturated current, can now be simply expressed as $$i = I_{HTO/H_2O} c_g V. \qquad (5)$$

In order to establish a correspondence between the current signal from the ionization chamber and the tritium activity in the pre-vaporized liquid water, let $c_w$ be the concentration of HTO in liquid water. The mass of water vapor at pressure p and temperature T in a detection volume V can be expressed simply as $$m = \frac{PVA_{H_2O}}{RT} \qquad (6)$$

where R is the ideal gas law constant and $A_{H_2O}$ is the molecular weight of water. Using the preceding equations we obtain the relationship for the tritium concentration in water $c_w$ in terms of the measured current i:

$$c_w = \frac{c_g V}{m} = \frac{i}{I_{HTO/H_2O}} \cdot \frac{RT}{PVA_{H_2O}}. \qquad (7)$$

The preceding relationship assumes that the vapor/liquid partition of tritium in tritiated water is negligible.

Assume that the detection limit for a bakeable ionization chamber is a current signal of 1 fA (1 femtoampere=$10^{-15}$ amperes). For a detection volume of 1 L ($10^{-3}$ m$^3$), water vapor pressure of 1 atm, monitor and vapor temperature of 250° C., and a $W_{H_2O(v)}$ value of 29.6 eV per ion pair, one obtains a corresponding detection limit of tritium in water of 2.1 µCi/L. From observation of equation 7 it is evident that the detection limit for tritium in water can be improved by increasing the detection volume and water vapor pressure and by lowering the measurable current signal. For example, a ten-fold increase in the detection volume will result in a tritium in water detection limit of 0.2 µCi/L while a doubling of the water vapor pressure would result in a further improvement to 0.1 µCi/L. Recently advances in current measurement circuitry suggest that a detection limit of 0.5 fA is achievable which would imply an ultimate tritium in water detection limit of 0.05 µCi/L. One might conservatively presume that such a detection system in reality might not do better than a factor of 5, which then suggests a practical detection limit of 0.25 µCi/L. It should be noted that one other change which could also improve the detection limit is an increase in the specific saturation current or alternatively introducing an electron multiplying gas in the water vapor, such as methane, which will effectively reduce the W value and thus improve the sensitivity of the detector.

EXAMPLES

Figure 2:
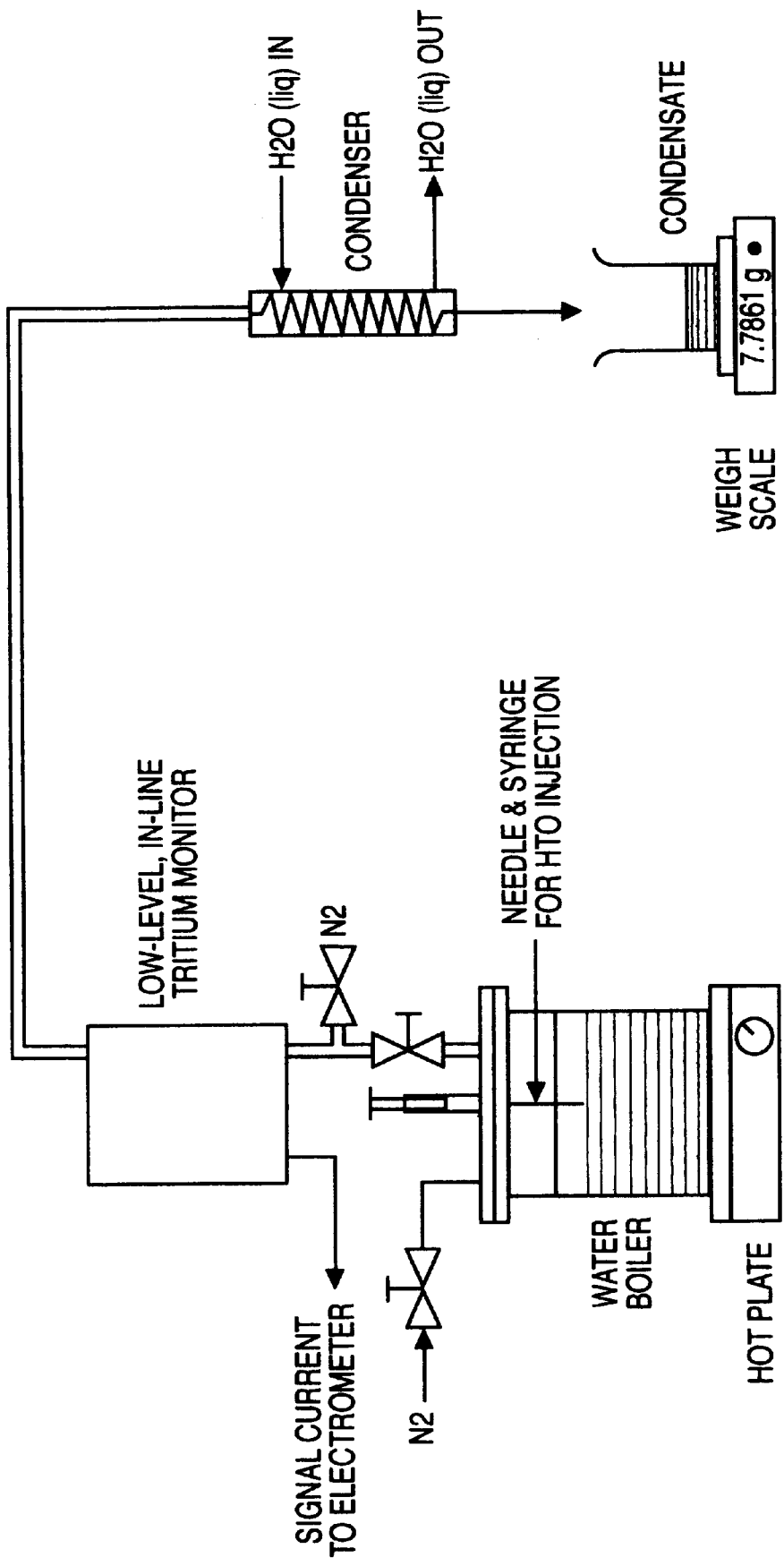
FIG. 2 is a schematic diagram of a preferred apparatus used in the examples to measure tritium levels in samples of water.
Figure 3:
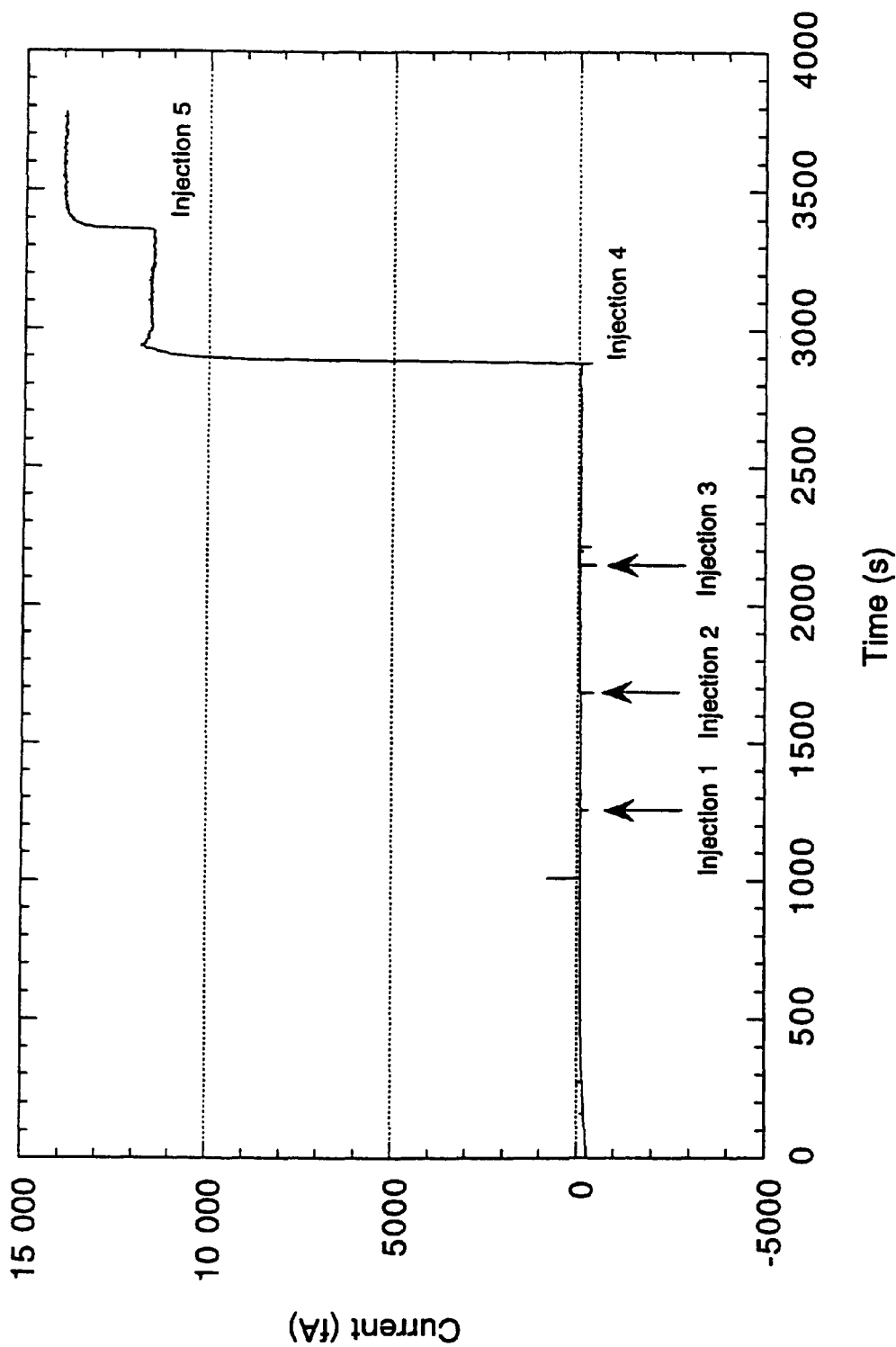
FIG. 3 is a plot of current against time for Example 1.
Figure 4:
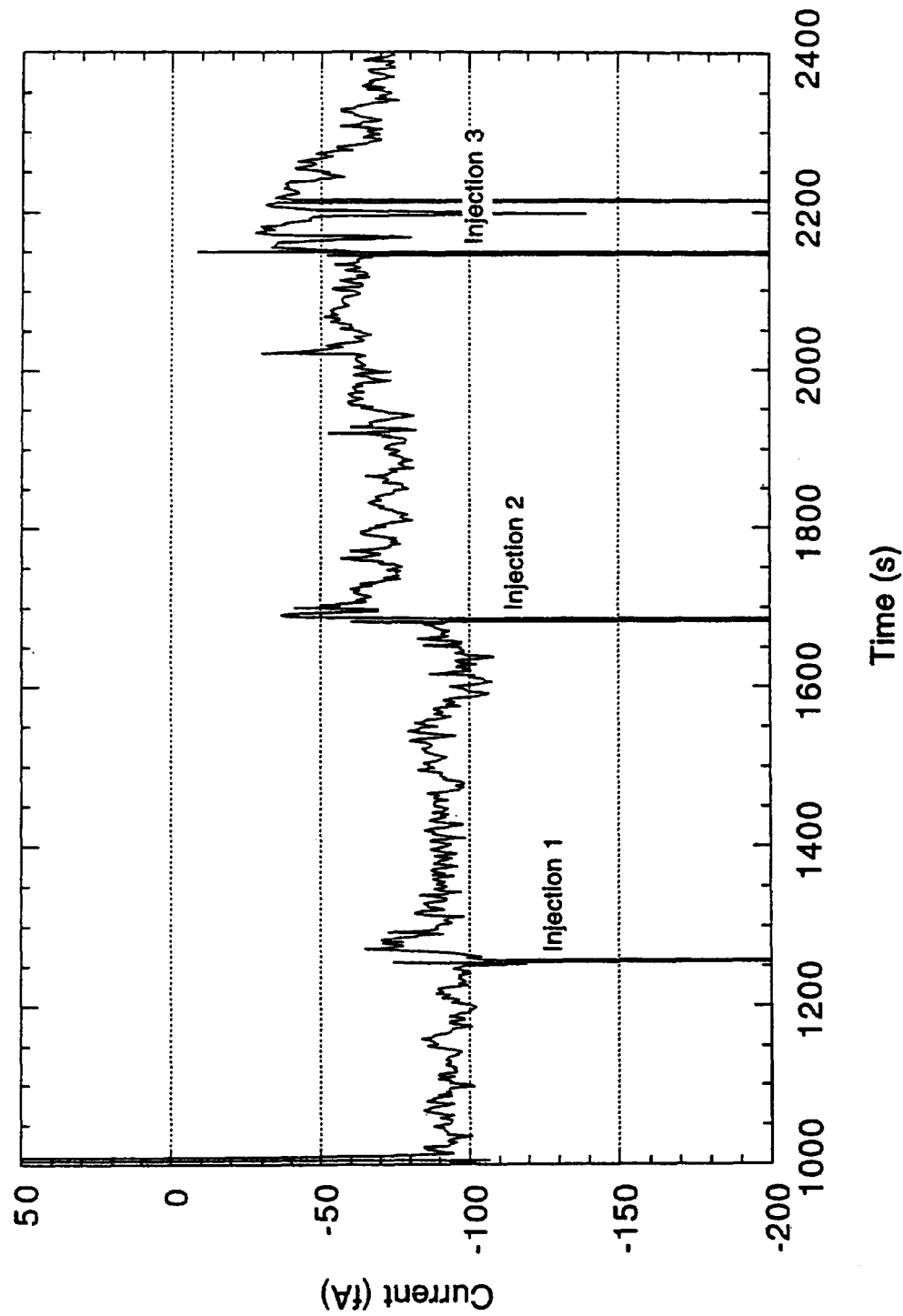
FIG. 4 is a more detailed view of a portion of the current-time plot of Example 1.

FIG. 2 is a schematic diagram of a simple experimental system designed to demonstrate the viability of using an ionization chamber for tritium-in-water detection. The system consists of a bakeable ionization chamber tritium monitor, a water boiler to vaporize liquid water, a septum on the boiler to permit injection of HTO$_{(l)}$ with a needle and syringe, a water cooled condenser to condense the dry water vapor, and a weigh scale to measure the rate of flow of water. The ionization chamber tritium monitor and the flow lines between it and the boiler and condenser are heated to ~250° C., thus ensuring the presence of dry water vapor and avoiding any condensation of water within the ionization chamber. The current signal from the ionization chamber is measured with a Keithley 617 electrometer wherein the collector is held at a bias of −100 V dc; the current-time data is collected by a data acquisition system. The peak-to-peak noise in the current signal is ~10 fA, implying a current detection limit of ~10 fA.

Each experiment involved pre-heating of the ionization chamber and the flow lines to and from it to a temperature of ~250° C. followed by heating of tritium-free deionized water in the boiler to a steady boil. Upon achieving a steady-state condition, the background current signal is noted and the corresponding condensate is analyzed for background tritium activity using a liquid scintillation counter. Subsequently, a small volume of tritiated water is injected via the septum into the boiling water and the ensuing response of the ionization chamber is observed. Once again, upon achieving a steady-state condition, the current signal is noted and the corresponding condensate is analyzed for tritium activity. This procedure is repeated for each additional injection of tritiated water. During the course of each experiment the rate of mass increase on the weigh scale is noted to obtain the rate of flow of water.

Experimental results for three experiments with progressively lower concentrations of tritium in water are shown in FIGS. 3 to 7 and in Tables 1 to 3. The figures show the ionization chamber current-time plots while the tables summarize the steady state data for each test. The respective flow rates of water in Examples 1, 2 and 3 are as follows: 3.5 mL H$_2$O(l)/min (4.4 L H$_2$O(g)/min), 3.1 mL H$_2$O(l)/min (3.9 L H$_2$O(g)/min), and 4.1 mL H$_2$O(l)/min (5.1 L H$_2$O(g)/min).

Example 1

A total of 5 separate tritium injections were carried out. The first three injections resulted in tritium-in-water concentrations of the order of a few tens of µCi/L, while the last two injections had concentrations of the order of tens of mCi/L. The current signals due to the first two injections (FIGS. 3 and 4) are largely mired in the noise of the instrument while the current signal following the third injection is becoming discernible. The current signals due to injections four and five are observed very clearly. The large spikes in the current-time plots corresponding to the injection of tritiated water are due to physical disturbances of the current signal conductor. The steady state data in Table 1 shows that following injections 3, 4 and 5, the tritium-in-water concentration as predicted by the ionization monitor signal is in good agreement with tritium activity in the condensate as measured by LSC.

Example 2

This was essentially a repetition of the first experiment, but carried out more carefully in order to observe the current response of the ionization chamber during the various stages of the test. Also, the temperature of the flow line between the ionization chamber and the condenser was elevated to 250° C. as opposed to 170° C. in Example 1; the temperatures of the ionization chamber and the flow line between the boiler and the ionization chamber remained unchanged at 250° C.

Figure 5:
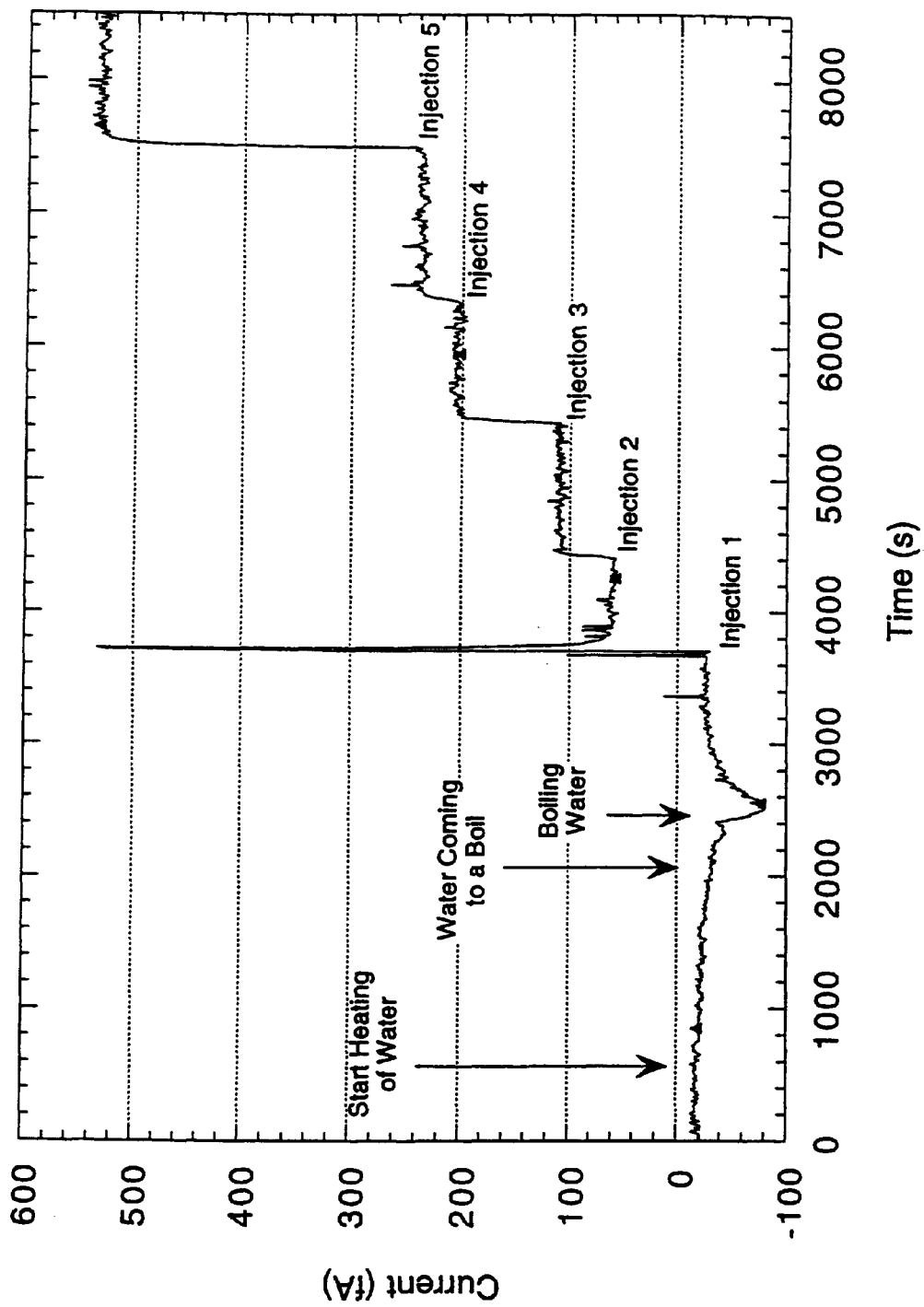
FIG. 5 is a plot of current against time for Example 2.
Figure 6:
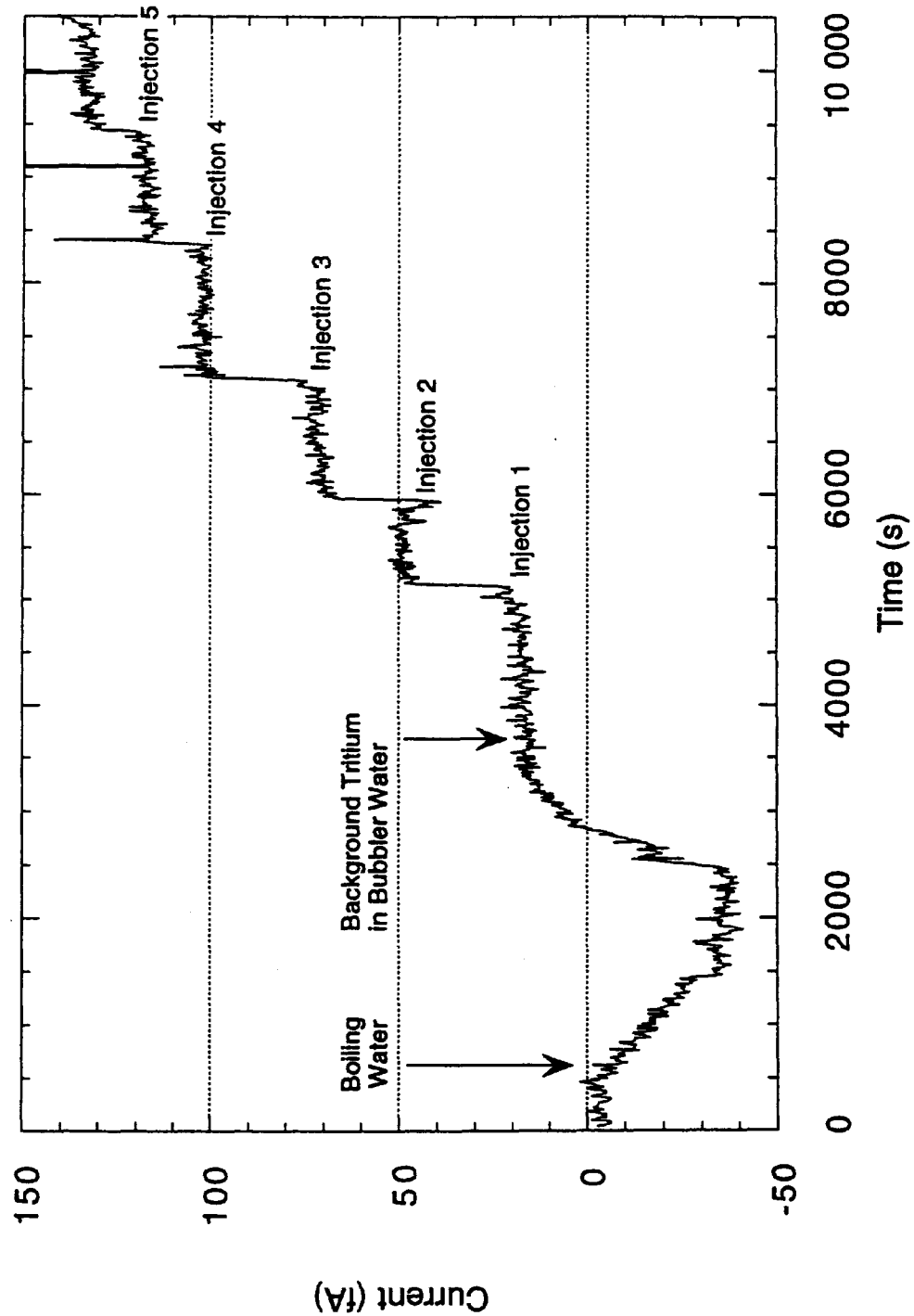
FIG. 6 is a plot of current against time for Example 3.
Figure 7:
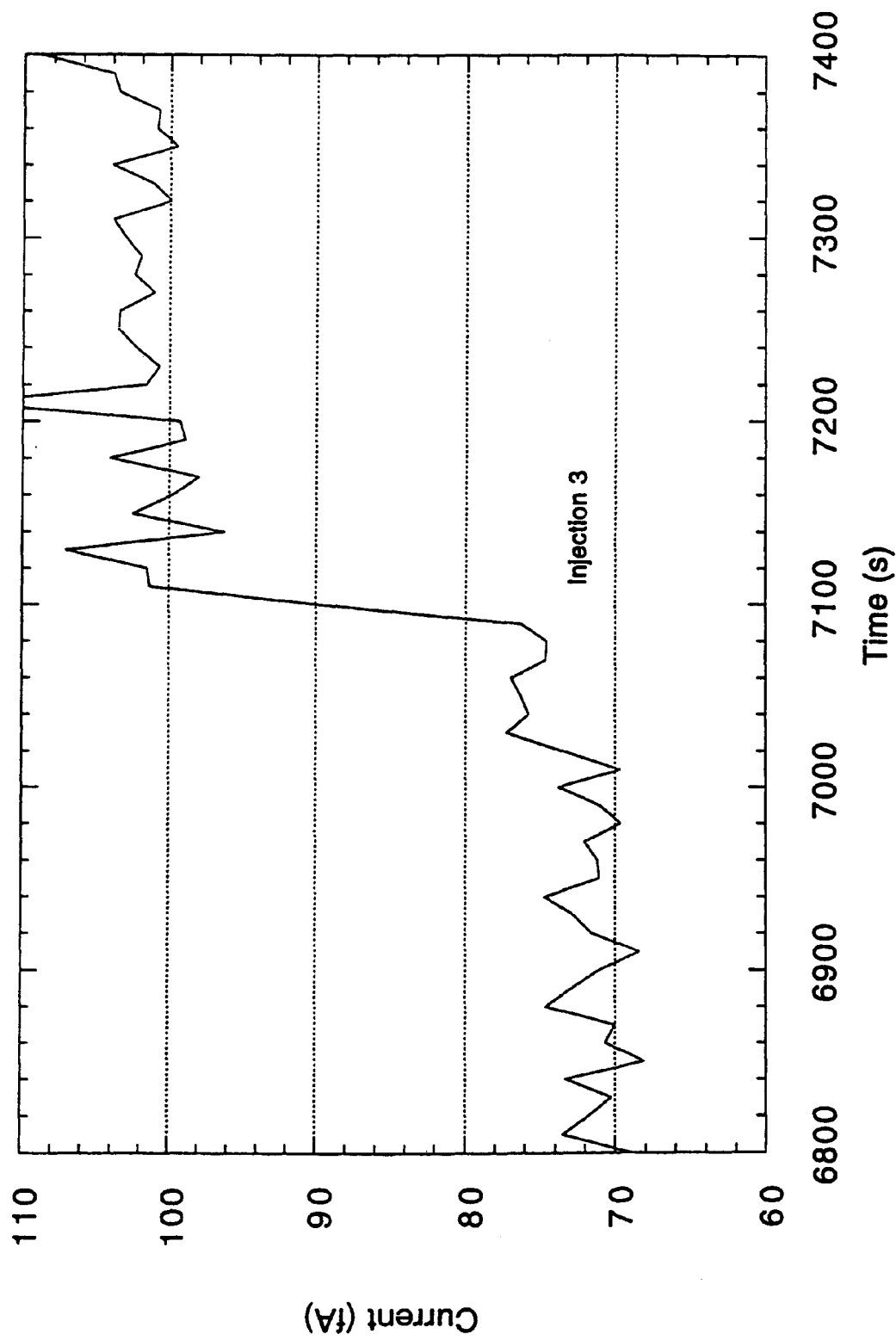
FIG. 7 is a more detailed view of a portion of the current-time plot of Example 3.

The current-time plot in FIG. 5 shows that as the water in the boiler comes to a boil the current signal begins to drop, followed by a sharp drop in the current to a minimum as the water begins to boil, and then the current signal begins to rise until it reaches a steady state value which corresponds to the steady state current signal prior to the heating of the water. This result indicates the occurrence of a leakage current at the electrical feedthrough in the ionization chamber as the system comes to a steady state operating condition. In particular, it is believed that while the monitor is at a temperature of 250° C., the high purity, glazed alumina ceramic feedthrough is at a lower temperature and therefore a site for the condensation of the vaporized water and thus the observed leakage current. However, as the water vapor continues to flow through the monitor, the feedthrough is convectively heated and in due course any condensed water on the surface of the feedthrough evaporates and hence the disappearance of the leakage current.

The current-time plot of FIG. 5 also shows that with the exception of injection 1 (due to physical disturbance of the current signal conductor), there are no large current spikes as observed in Example 1. Upon introduction of tritium into the boiling water a monotonic increase in the current signal is observed for each of the injections. The current-time plot along with the corresponding data in Table 2 show that tritium concentrations of less than 70 µCi/L are clearly measurable.

Example 3

The current-time plot for Example 3 (FIG. 6) shows similar results to that observed in Example 2 with the exception that the incremental concentrations of tritium-in-water are smaller. It is also interesting to note that in this example the boiler water at the start of the experiment was found not to be free of tritium as evidenced by the non-zero net current signal from the ionization chamber. In fact, LSC analysis of the condensate confirmed this result; that is, a predicted background tritium-in-water concentration of 44 µCi/L compared to the condensate activity of 37 µCi/L (see Table 3). As with Examples 1 and 2, Example 3 shows good agreement between the ionization chamber predicted concentrations and the condensate concentrations. Also, in this experiment it is evident that a tritium-in-water concentration of less than ~30 µCi/L is measurable. Furthermore, in FIG. 6 the instrument time response is observed to be of the order of less than 10 s (~20 s to realize a change of >90% of the steady state signal).

The ratio of the tritium activities as predicted by the tritium monitor to that measured in the condensate is of the order of unity ±~15%. Vapor/liquid partition of tritium in tritiated water will only account for a variation of a few (~3) percent. However, closer observation of the ratios shows that the ratio is usually less than unity, implying that the ionization chamber is underestimating the actual concentration of tritium as measured by LSC. It is believed that this attenuation in current signal is likely due to the presence of some liquid water droplets in the water vapor stream flowing through the detector. It is expected that application of the preferred apparatus will reduce or eliminate this effect.

In conclusion, the above proof-of-principle experimental results demonstrate the viability of the method and apparatus of the invention for detection of tritium-in-water to concentrations as low as ~20 µCi/L and time constants of less than 10 seconds. However, with present day improvements in current measuring circuitry, detection limits of less than 250 nCi/L can be achieved.

TABLE 1

Example 1: Tritium-in-water monitoring using water vapor in a heated, in-line, ionization chamber tritium monitor (monitor background-95fA).

| Injection | Activity in Condensate as per LSC (µCi/L) | Net Ionization Chamber Tritium Monitor Signal (fA) | Activity in Water as per Tritium Monitor (µCi/L) | Ratio of Activities: Tritium Monitor to LSC |
|---|---|---|---|---|
| 1 | 5.5 | 10 | 21 | 3.8 |
| 2 | 14 | 35 | 73 | 5.2 |
| 3 | 50 | 35 | 73 | 1.5 |
| 4 | 22420 | 11745 | 24550 | 1.1 |
| 5 | 27120 | 14055 | 29380 | 1.1 |

TABLE 2

Example 2: Tritium-in-water monitoring using water vapor in a heated, in-line, ionization chamber tritium monitor (monitor background-25fA).

| Injection | Activity in Condensate as per LSC (µCi/L) | Net Ionization Chamber Tritium Monitor Signal (fA) | Activity in Water as per Tritium Monitor (µCi/L) | Ratio of Activities: Tritium Monitor to LSC |
|---|---|---|---|---|
| 1 | 241 | 83 | 177 | 0.74 |
| 2 | 358 | 134 | 286 | 0.80 |
| 3 | 584 | 231 | 491 | 0.84 |
| 4 | 692 | 263 | 560 | 0.81 |
| 5 | 1554 | 557 | 1187 | 0.76 |

TABLE 3

Example 3: Tritium-in-water monitoring using water vapor
in a heated, in-line, ionization chamber tritium monitor
(monitor background-3fA).

| Injection | Activity in Condensate as per LSC ($\mu$Ci/L) | Net Ionization Chamber Tritium Monitor Signal (fA) | Activity in Water as per Tritium Monitor ($\mu$Ci/L) | Ratio of Activities: Tritium Monitor to LSC |
|---|---|---|---|---|
| none | 37 | 20 | 44 | 1.17 |
| 1 | 130 | 52 | 111 | 0.86 |
| 2 | 192 | 76 | 161 | 0.84 |
| 3 | 250 | 106 | 226 | 0.90 |
| 4 | 300 | 121 | 257 | 0.86 |
| 5 | 333 | 138 | 293 | 0.86 |

The invention has been described throughout this application as being applicable to measurement of tritium levels in water. However, it will be appreciated that the principles of the present invention are readily applicable to the measurement of tritium levels in aqueous liquids other than water, for example in urine as disclosed by Robinson, and may also be applicable to the measurement of tritium levels in non-aqueous liquids.

Furthermore, although the preferred embodiments of the invention have been described in relation to the monitoring of tritium in water in nuclear reactor systems, it is to be appreciated that the method and apparatus of the present invention could also be used to monitor tritium levels in water discharged from other sources into sewers and natural waterways, for example water discharged from plumbing pipes of nuclear power stations. The method and apparatus of the invention may also permit monitoring of tritium levels in natural bodies of waters such as lakes, rivers and streams.

Although the invention has been described in relation to certain preferred embodiments, it is to be appreciated that it is not limited thereto. Rather, the present invention includes all embodiments as may fall within the scope of the following claims.

What is claimed is:

1. An apparatus for continuously monitoring tritium content in a stream of water flowing through a conduit, said apparatus comprising:

(a) an inlet connected to said conduit, said inlet adapted to receive a portion of said stream of water from said conduit;

(b) centrifuging means connected to said inlet for centrifuging said portion of said stream of water diverted from said conduit;

(c) aspirating means adapted to generate a mist of water from said portion of said stream of water being centrifuged;

(d) heated conduit means having a first end and a second end, said first end adapted to receive said mist from said aspirating means, said conduit means being heated to a temperature sufficient, and being of sufficient length, to convert said mist to a dry water vapor containing substantially no liquid water as it passes from said first end to said second end;

(e) tritium detection means comprising a volume detection device adapted to detect $\beta$-decay of tritium atoms in said water vapor and to generate a signal which is representative of said tritium content of said stream of water flowing through said conduit, said tritium detection means comprising a chamber having an inlet and an outlet, said inlet receiving said dry water vapor from a gas vortex, said chamber being heated to a temperature at which there is substantially no condensation of said water vapor inside said chamber;

(f) condensor means receiving said water vapor from said tritium detection means and cooling it to a temperature at which it is condensed to liquid water; and (g) outlet means through which condensed water leaves the apparatus.

2. The apparatus of claim 1, wherein said volume detection device is selected from the group comprising ionization chamber detection means, gas scintillation counting detection means and proportional detection means.

3. The apparatus of claim 2, wherein said volume detection device additionally comprises gas electron multiplier means.

4. The apparatus of claim 1, wherein said apparatus further comprises gas pressurization means between said gas vortex and said tritium detection means, said gas pressurization means increasing the pressure of the water vapor before it enters the chamber of the detection means.

5. The apparatus of claim 4, wherein said gas pressurization means increases the pressure of the water vapor to the range of from about 1 to about 3 atmospheres.

6. The apparatus of claim 1, further comprising a gas vortex connected to said second end of said heated conduit means and being adapted to remove residual water droplets from said water vapor.

7. The apparatus of claim 2, wherein said volume detection device comprises gas scintillation counting detection means and wherein said apparatus further comprises a gas inlet through which a scintillating gas is added to said dry water vapor immediately before it enters the chamber of the detection means.

* * * * *